(12) United States Patent
Alonso et al.

(10) Patent No.: US 10,046,044 B2
(45) Date of Patent: Aug. 14, 2018

(54) **PREVENTION OF *PERTUSSIS* USING ADENYLATE CYCLASE DEFICIENT *BORDETELLA* STRAINS**

(71) Applicants: National University of Singapore, Singapore (SG); Institut Pasteur de Lille, Lille (FR); Institut National de la Santé et de la Recherche Médicale (INSERM), Paris (FR)

(72) Inventors: Sylvie Claudette Alonso, Singapore (SG); Rui Fen Annabelle Lim, Singapore (SG); Camille Locht, Brussels (BE)

(73) Assignees: National University of Singapore, Singapore (SG); Institut National de la Santé et de la Recherche Médicale (INSERM), Paris (FR); Institut Pasteur de Lille, Lille (FR)

( * ) Notice: Subject to any disclaimer, the term of this patent is extended or adjusted under 35 U.S.C. 154(b) by 0 days.

(21) Appl. No.: 15/477,562

(22) Filed: Apr. 3, 2017

(65) Prior Publication Data

US 2017/0202944 A1   Jul. 20, 2017

Related U.S. Application Data

(62) Division of application No. 14/870,487, filed on Sep. 30, 2015, now Pat. No. 9,655,959.

(60) Provisional application No. 62/058,172, filed on Oct. 1, 2014.

(51) Int. Cl.
*A61K 39/02*  (2006.01)
*A61K 39/00*  (2006.01)

(52) U.S. Cl.
CPC ...... *A61K 39/099* (2013.01); *A61K 2039/522* (2013.01)

(58) Field of Classification Search
CPC .......... A61K 2039/522; A61K 2039/10; A61K 2039/577; A61K 35/74; A61K 39/39; A61K 39/099; C12N 1/36
See application file for complete search history.

(56) References Cited

U.S. PATENT DOCUMENTS 6,660,261 B1     12/2003  Mielcarek
9,655,959 B2 *   5/2017   Alonso ............... A61K 39/099

OTHER PUBLICATIONS

Zeddeman, A. et al: "Investigations into the emergence of pertactin-deficient Bordetella pertussis isolates in six European countries, 1996 to 2012," Research Articles, Aug. 21, 2014, pp. 1-11; «www.eurosurveillance.org.».
Thorstensson, R. et al: "A Phase I Clinical Study of a Live Attenuated Bordetella pertussis vaccine—BPZE1; A Single Centre, Double-Blind, Placebo-Controlled, Dose-Escalating Study of BPZE1 Given intranasally to healthy adult male volunteers," PLOS ONE, Jan. 2014, vol. 9, No. 1:10.

* cited by examiner

*Primary Examiner* — Padmavathi Baskar
(74) *Attorney, Agent, or Firm* — Stanley A. Kim

(57) ABSTRACT

A CyaA-deficient *B. pertussis* mutant was constructed and used in a vaccine. The *pertussis*-specific antibody profile and Th17 response induced by vaccination with the mutant was surprisingly comparable to that induced by *B. pertussis* strains not deficient in CyaA.

9 Claims, 5 Drawing Sheets

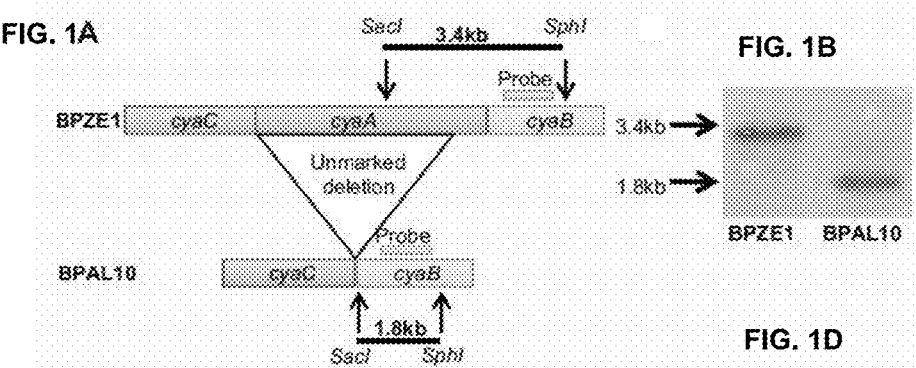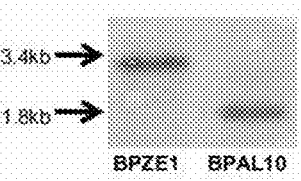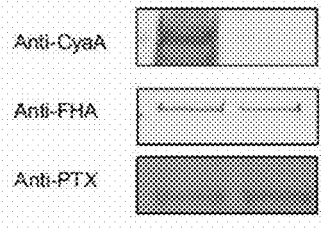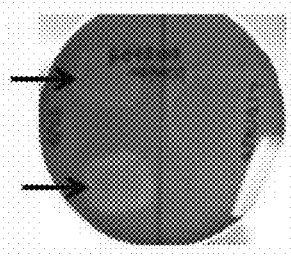

FIG. 5

```
SEQUENCE LISTING

<160> NUMBER OF SEQ ID NOS: 4

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tttctagagg cggtgccccg gcctcg                                            26

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttgagctctc gcaccgacgc aaccggtg                                          28

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttgagctcag cgccgtgaat cacggccc                                          28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttaagcttag caaggcaacg ccgccagc                                          28
```

PREVENTION OF *PERTUSSIS* USING ADENYLATE CYCLASE DEFICIENT *BORDETELLA* STRAINS

CROSS-REFERENCE TO RELATED APPLICATIONS

The present application is a divisional application of U.S. patent application Ser. No. 14/870,487 filed on Sep. 30, 2015, which claims the priority of U.S. provisional patent application Ser. No. 62/058,172 filed on Oct. 1, 2014.

SEQUENCE LISTING

The instant application contains a Sequence Listing which has been submitted electronically in ASCII format and is hereby incorporated by reference in its entirety. Said ASCII copy, created on Sep. 28, 2015, is named 7056-0062_SL.txt and is 1,212 bytes in size.

STATEMENT AS TO FEDERALLY SPONSORED RESEARCH

Not applicable.

FIELD OF THE INVENTION

The invention relates generally to the fields of microbiology, immunology, vaccinology, sero-epidemiology, biochemistry and medicine. More particularly, the invention relates to mutated strains *Bordetella pertussis* having deficient adenylate cyclase (CyaA) and their use as vaccines.

BACKGROUND

Despite high vaccination coverage, *Bordetella pertussis* infection remains endemic and reports of increasing incidence in Australia, Canada, and Europe have been accumulating for the past twenty years. 2012 was the year with the highest whooping cough incidence in US and comparable outbreaks occurred also in the UK and Netherlands, in proportion of inhabitant numbers. Adaptation of the circulating *pertussis* strains to the vaccines, as well as the waning and/or suboptimal efficacy of vaccine-mediated immunity during adolescence has been proposed to account for resurgence, with infected adolescent and adult populations being the major transmitters of disease in community representing a potential reservoir for disease transmission to young children who are yet to be fully vaccinated. Furthermore, with the changing epidemiology, *pertussis* is increasingly becoming a real burden also in adults that experience long-lasting and very heavy cough periods of duration in weeks to months. This underscores the need to pursue research efforts on this disease in order to provide suitable protection to the most vulnerable populations.

One approach to developing new vaccines to prevent *B. pertussis* infection is to use live but attenuated *Bordetella* bacteria as an antigenic agent. Creating such vaccines remains a challenging endeavor because, in order to be safe and effective, the attenuation must remove toxicity while still preserving sufficient antigenicity and viability. Deletion or mutation of various *B. pertussis* components can be lethal to the bacteria, can render the bacteria unable to colonize a subject, and/or unable to induce a sufficiently protective immune response.

Previously, after much work and numerous failures, a highly attenuated *B. pertussis* strain named BPZE1 [deposited with the Collection Nationale de Cultures de Microorganismes (CNCM, Institut Pasteur, 25 Rue du Docteur Roux, F-75724, Paris, Cedex 15, France) on Mar. 9, 2006 under the number CNCM I-3585] was developed. This strain produces enzymatically inactive *pertussis* toxin (PTX), no dermonecrotic toxin (DNT), and only trace amounts of tracheal cytotoxin (TCT). It was also shown to be genetically stable and safe in preclinical models and a 12 subject clinical trial. Given that *B. pertussis* virulence factors have evolved to promote colonization and prevent infection clearance (e.g., PTX inhibits neutrophils/macrophage recruitment and TCT induces ciliostasis), BPZE1's ability to colonize the lung was impaired. Nonetheless, it was surprisingly found that intranasally (i.n.) administered BPZE1 was able to colonize the lungs of mice sufficiently to induce a strong protective humoral and cellular immunity.

SUMMARY

Described herein is the development of a new live, attenuated *B. pertussis* strain that is useful for inducing protective immune responses against *B. pertussis* infection. The newly developed strain is deficient in adenylate cyclase toxin (CyaA) as well as PTX, DNT, and TCT. CyaA is a polypeptide that is synthesized as an inactive protoxin which, after posttranslational fatty acylation, is converted to an active toxin. The C-terminal domain of the active toxin binds to target cell membranes allowing the N-terminal catalytic domain to enter the target cell's cytosol where it is activated by $Ca^{2+}$/calmodulin to catalyze the conversion of cellular ATP into cAMP. Increased cAMP interferes with the signaling pathways in immune cells (including macrophages and neutrophils) and reduces phagocytic activity. CyaA has been previously reported to be an important colonization factor for *B. pertussis* that helps initiate infection. Because the newly developed strain is deficient in two key phagocyte-neutralizing factors, CyaA and PTX, and BPZE is already impaired in its ability to colonize, it was surprising to discover that this quadruple mutant was also able to sufficiently colonize the lungs of subjects to induce protective immunity against later challenges with wild-type *B. pertussis*.

Accordingly, in one aspect, the invention features a live attenuated *Bordetella* strain which has been engineered to reduce or remove CyaA activity while retaining the ability to colonize the lungs of a subject and induce protective immunity against later challenges with wild-type *B. pertussis*. Preferably the live attenuated *Bordetella* strain also has been engineered to reduce or remove the activity of at least one (e.g., 1, 2, or 3) of: PTX, DNT, and TCT.

It another aspect, the present invention includes a method of using a live attenuated *Bordetella* strain which has been engineered to reduce or remove CyaA activity and at least one (1, 2, or 3) of PTX activity, DNT activity, and TCT activity to elicit an immune response which protects a mammalian subject (e.g., a human being) against *B. pertussis* infection.

In the various aspects of the invention, the live attenuated *Bordetella* strain which has been engineered to reduce or remove CyaA, PTX, DNT, and TCT activity is BPAL10 [deposited in accordance with the requirements of the Budapest Treaty with the National Measurement Institute ("NMI"), 1/153 Bertie Street, Port Melbourne, Victoria, Australia 3207 on Oct. 23, 2015 under accession number V15/032164.

Also within the invention is a vaccine including a pharmaceutically acceptable carrier and a live attenuated *Bor-*

*detella* strain that has been rendered deficient in functional CyaA, PTX, dermonecrotic toxin (DNT), and tracheal cytotoxin (TCT), but retains the ability to colonize a mammalian subject's lungs and induce a protective immune response against *Bordetella* infection. The strain can include a gene encoding CyaA which has been mutated such that the strain fails to produce CyaA and/or a gene encoding PTX which has been mutated such that the strain fails to produce PTX. The strain can also lack a gene encoding functional DNT and/or a functional wild-type ampG gene (which can be replaced by a heterologous ampG gene).

Further within the invention is a method of protecting a mammalian subject from developing *pertussis*. This method includes the step of administering to the mammalian subject a vaccine including a sufficient amount of one or more of the live attenuated *Bordetella* strains described above to elicit immune response that prevents the mammalian subject from developing *pertussis* after exposure to *B. pertussis*.

Unless otherwise defined, all technical terms used herein have the same meaning as commonly understood by one of ordinary skill in the art to which this invention belongs. Commonly understood definitions of biological terms can be found in Rieger et al., Glossary of Genetics: Classical and Molecular, 5th edition, Springer-Verlag: New York, 1991; and Lewin, Genes V, Oxford University Press: New York, 1994.

As used herein, the abbreviation "CyaA" refers to adenylate cyclase toxin, which is a virulence factor synthesized by Bordetellae. CyaA is a polypeptide that is synthesized as an inactive protoxin which, after posttranslational fatty acylation, is converted to an active toxin. The C-terminal domain of the active toxin binds to target cell membranes allowing the N-terminal catalytic domain to enter the target cell's cytosol where it is activated by Ca2+/calmodulin to catalyze the conversion of cellular ATP into cAMP. Increased cAMP interferes with the signaling pathways in immune cells (including macrophages and neutrophils) and reduces reduce their phagocytic activity.

As used herein, the abbreviation "PTX" refers to *pertussis* toxin, which synthesizes and secretes an ADP-ribosylating toxin. PTX is composed of polypeptides S1 to S5, the enzymatically active moiety is called S1. PTX has a 34 amino acid signal sequence, while the mature chain consists of amino acids 35 to 269. PTX is the major virulence factor expressed by *B. pertussis*. The A moiety of these toxins exhibit ADP-ribosyltransferase activity and the B portion mediates binding of the toxin to host cell receptors and the translocation of A to its site of action.

As used herein the abbreviation "DNT" refers to *pertussis* dermonecrotic toxin, which is a heat labile toxin that induces localized lesions in mice and other laboratory animals when it is injected intradermally. It is lethal to mice when it is injected in low doses intravenously, and is considered to be a virulence factor for the production of turbinate atrophy in porcine atrophic rhinitis.

As used herein the abbreviation "TCT" refers to tracheal cytotoxin, which is a virulence factor synthesized by Bordetellae. TCT is a peptidoglycan fragment and has the ability to induce interleukin-1 production and nitric oxide synthase. It has the ability to cause stasis of cilia and has lethal effects on respiratory epithelial cells.

The term "functional" when referring to a toxin means that the toxin retains wild-type activity. For example, a *Bordetella* strain that has been rendered deficient in functional CyaA, PTX, DNT, or TCT exhibits less than 50% (e.g., less than 50, 40, 30, 20, 10, 5, 4, 3, 2, or 1%) of at least one of that toxin's native activity described in the preceding four paragraphs.

The term "mammal", "mammalian subject" or "subject" encompasses any of various warm-blooded vertebrate animals of the class Mammalia, including human beings, characterized by a covering of hair on the skin and, in the female, milk-producing mammary glands for nourishing the young.

The term "attenuated" means a weakened, less virulent *Bordetella* strain that is capable of stimulating an immune response and creating protective immunity, but does not cause significant illness.

The term "*Bordetella* strain" encompasses strains from *Bordetella pertussis, Bordetella parapertussis* and *Bordetella bronchiseptica*.

The expression "*Bordetella* infection" means an infection caused by at least one of the three following strains: *Bordetella pertussis, Bordetella parapertussis* and *Bordetella bronchiseptica*.

By "child" is meant a person or a mammal between 6 months and 12 years of age.

By the term "newborn" is meant, a person or a mammal that is between 1 day old and 24 weeks of age.

The term "treatment" as used herein is not restricted to curing a disease and removing its causes but particularly covered means to cure, alleviate, remove or lessen the symptoms associated with the disease of interest, or prevent or reduce the possibility of contracting any disorder or malfunction of the host body.

The terms "protection" and "prevention" are used herein interchangeably and mean that an infection by *Bordetella* is impeded.

"Prophylaxis" means that to prevent or reduce the pathological effects or symptoms of an infection.

The term "immunogenic composition" means that the composition can induce an immune response and is therefore antigenic. By "immune response" means any reaction by the immune system. These reactions include the alteration in the activity of an organism immune system in response to an antigen and may involve, for example, antibody production, induction of cell-mediated immunity, complement activation or development of immunological tolerance.

Although methods and materials similar or equivalent to those described herein can be used in the practice or testing of the present invention, suitable methods and material are described below. All publications and patent applications mentioned herein are incorporated by reference in their entirety. In the case of conflict, the present specification, including definitions will control. In addition, the particular embodiments discussed below are illustrative only and not intended to be limiting.

DESCRIPTION OF THE DRAWINGS

FIG. 1A is a schematic diagram of the probe design for Southern blot analysis of BPAL10. Restriction enzymes, SacI and SphI are indicated by arrows.

FIG. 1B is a Southern blot analysis of the CyaA locus in BPZE1 and BPAL10.

FIG. 1C is a Western blot analysis of CyaA, FHA and PTX production in whole cell extracts and supernatants from BPZE1 and BPAL10.

FIG. 1D is a photograph showing hemolytic activity of BPZE1 and BPAL10 on blood agar observed upon incubation at 37° C. for 3 days.

FIG. 5 is a series of graphs showing challenge experiments with virulent *B. pertussis*. Three week-old BALB/c mice were intranasally immunized with PBS (naive) (black bar), BPZE1 (openbar) or BPAL10 (gray bar) using two doses, $5 \times 10^5$ CFU (A) or $5 \times 10^3$ CFU (B), and challenged with $5 \times 10^6$ CFU of virulent *B. pertussis* BPSM one month post-immunization. At the indicated time points, 4 animals per group were euthanized and their lungs were harvested and processed for colony counting. The results are expressed as the mean of CFU from 4 mice (+/−standard deviations). The dashed line represents the detection limit of the number of CFU present in the lungs. P value of <0.01 (**) compared to BPZE1 mice were considered significant.

DETAILED DESCRIPTION

Figure 2:
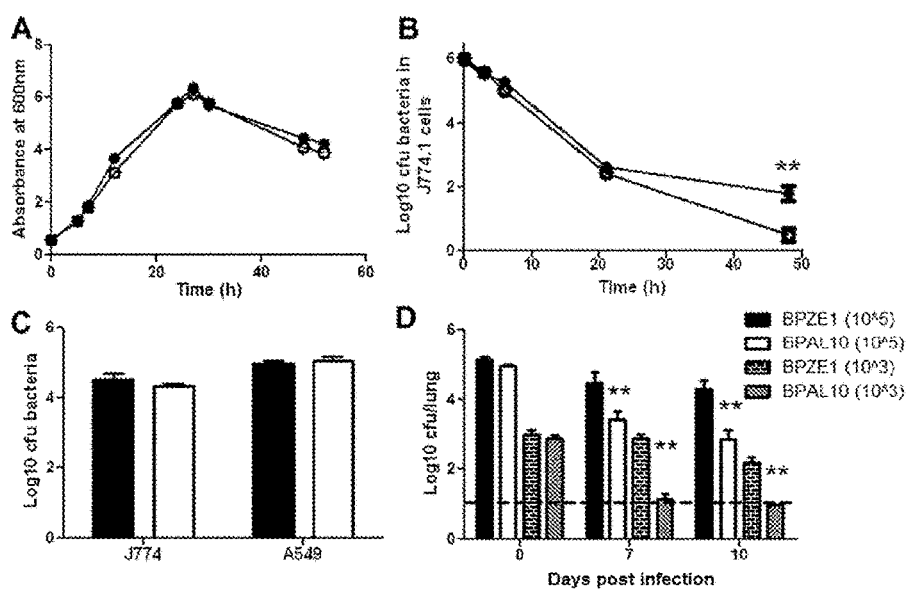
FIG. 2 is a series of graphs showing the phenotypic characterization of BPAL10. (A) In vitro growth kinetic of BPAL10 (open circle) and BPZE1 (solid circle) in SS liquid culture. Exponential liquid bacterial pre-cultures in SS medium were used to inoculate a fresh culture medium at an initial OD600 nm of 0.5. Growth of bacteria was monitored over time at the indicated time points. (B) In vitro cell invasion assay of BPAL10 (open circle) and BPZE1 (solid circle) in J774.A1 cells. The infected cells (MOI 20) were incubated for 1 h at 37° C. and 5% $CO_2$, washed and further incubated with gentamycin for 2 h to remove extracellular bacteria. Cells were washed, lysed and appropriate dilutions were plated for colony counting. P values of <0.01 () compared to BPZE1-immunized mice were considered significant. Each sample was performed in quadruplicate. The experiment was repeated twice independently. (C) In vitro adherence of BPAL10 (open bar) and BPZE1 (black bar) to murine macrophage-like J774.A1 cells and human pulmonary epithelial A549 cells as indicated. $2 \times 10^5$ mammalian cells per well were infected with BPAL10 or BPZE1 at MOI 20, incubated for 1 h at 4° C., washed, lysed, and appropriate dilutions were plated for colony counting. Each sample was performed in quadruplicate. The experiment was repeated twice independently. (D) Lung colonization profile of BPAL10 in 3 week-old BALB/c mice. Three week-old BALB/c mice were administered intranasally with either $5 \times 10^5$ CFU or $5 \times 10^3$ CFU of BPAL10 or BPZE1 as indicated. At the indicated time points, 4 mice per group were euthanized and their lungs were processed for colony counting. The results are expressed as means (±standard error) CFUs from 4 mice per group per time point, and are representative of two independent experiments. P values <0.01 () compared to BPZE1-immunized mice were considered significant. The dashed line represents the detection limit of the number of CFU present in the lungs.

Described herein are new *Bordetella* strains and methods of using such strains to generate protective immune responses against infectious agents. The present invention is not limited to only the mutants described above. Other additional mutations can be undertaken such as lipopolysaccharide (LPS) deficient mutants, filamentous hemagglutinin (FHA), and any of the bvg-regulated components.

General Methods

Methods involving conventional microbiological, immunological, molecular biological, and medical techniques are described herein. Microbiological methods are described in Methods for General and Molecular Microbiology (3d Ed), Reddy et al., ed., ASM Press. Immunological methods are generally known in the art and described in methodology treatises such as Current Protocols in Immunology, Coligan et al., ed., John Wiley & Sons, New York. Techniques of molecular biology are described in detail in treatises such as Molecular Cloning: A Laboratory Manual, 2nd ed., vol. 1-3, Sambrook et al., ed., Cold Spring Harbor Laboratory Press, Cold Spring Harbor, N.Y., 2001; and Current Protocols in Molecular Biology, Ausubel et al., ed., Greene Publishing and Wiley-Interscience, New York. General methods of medical treatment are described in McPhee and Papadakis, Current Medical Diagnosis and Treatment 2010, 49th Edition, McGraw-Hill Medical, 2010; and Fauci et al., Harrison's Principles of Internal Medicine, 17th Edition, McGraw-Hill Professional, 2008.

*Bordetella* Strains with Reduced or Removed CyaA and PTX Activity

The vaccines and methods described herein are based on live attenuated *Bordetella* strains that have been rendered deficient in functional virulence factors including CyaA and PTX, but retain the ability to colonize a mammalian subject's lungs and induce a protective immune response against *Bordetella* infection. Preferably such strains have also been rendered deficient in functional DNT and/or TCT. The strains can include a gene encoding CyaA which has been mutated such that the strain fails to produce functional CyaA and/or a gene encoding PTX which has been mutated such that the strain fails to produce functional PTX. The strains can also lack a gene encoding functional DNT and/or a functional wild-type ampG gene (which can be replaced by a heterologous ampG gene).

The live attenuated *Bordetella* strains described above can be made by methods known in the art such as those described in the Examples section below. The starting strain can be any suitable *Bordetella* species. Examples of *Bordetella* species include *B. pertussis*, *B. parapertussis*, and *B. bronchiseptica*. *B. pertussis* is preferred for use as the starting strain for vaccines and methods for preventing *pertussis* infection. A number of suitable *Bordetella* strains for use as starting strains are available from established culture collections (e.g., the American Type Culture Collection in Manassas, Va.) or can be isolated from natural reservoirs (e.g., a patient having *pertussis*) by known techniques (e.g., Aoyama et al., Dev. Biol. Stand, 73:185-92, 1991).

A variety of methods are known in the art for attenuating an infectious bacterial strain. These include passaging the strain in vitro until virulence is lost, non-specific chemical mutagenesis followed by screening and selection based on phenotype, and using targeted molecular biology techniques such as those described in the Examples section below (including allelic exchange) and in Methods for General and Molecular Microbiology (3d Ed), Reddy et al., ed., ASM Press. Using these methods, the genes encoding CyaA, PTX, and/or DNT can be deleted or mutated to an enzymatically inactive form (which is preferred where it is desired to retain the toxin's antigenicity). TCT production can be significantly (e.g., > than 99.99, 99.90, 99.8, 99.7, 99.6, 99.5, 99.0, 98, 97, 96, 95, or 90%) reduced by replacing the native ampG gene (unlike other species, *B. pertussis* ampG does not actively recycle TCT-containing peptidoglycan) with a heterologous (e.g., from *E. coli* or another gram negative species) ampG gene, or by mutating the native ampG gene such that it is active at recycling peptidoglycan.

Modification of a starting strain to reduce or remove toxin activity can be confirmed by sequencing the genomic DNA or genes encoding the toxins of the modified strains. Southern, Northern, and/or Western blotting might also be used to confirm that the target genes have been deleted or that expression of the target proteins has been reduced or removed. Enzyme activity can also be evaluated to confirm reduction or removal of toxin activity. Once the modifications have been confirmed, the modified strains can be tested for the ability to colonize a subject and to induce protective immunity against *Bordetella* infection by known methods such as those described in the Examples section below.

Vaccines

The live attenuated *Bordetella* strains described herein can be used in vaccines that protect a mammalian subject from developing a *Bordetella* infection (e.g., *pertussis*) or at least reduce the symptoms of such an infection. For use in a vaccine, the live attenuated *Bordetella* strains are formulated with a pharmaceutically acceptable excipient. Examples of pharmaceutically acceptable excipients include, e.g., buffered saline solutions, distilled water, emulsions such as an oil/water emulsion, various types of wetting agents sterile solutions, and the like.

The vaccines can be packaged in unit dosage form for convenient administration to a subject. For example, a single dose of between $1\times10^4$ to $1\times10^7$ (e.g., $1\times10^4$, $5\times10^4$, $1\times10^5$, $5\times10^5$, $1\times10^6$, $5\times10^6$, or $1\times10^7$ +/−10, 20, 30, 40, 50, 60, 70, 80, or 90%) live bacteria of the selected attenuated *Bordetella* strain and any excipient can be separately contained in packaging or in an administration device. The vaccine can be contained within an administration device such as a syringe, spraying device, or insufflator.

Methods of Eliciting Immune Responses to Protect Against *Pertussis*

The vaccines described herein can be administered to a mammalian subject (e.g., a human being, a human child or neonate, a human adult, a human being at high risk from developing complications from *pertussis*, a human being with lung disease, and a human being that is or will become immunosuppressed) by any suitable method that deposits the bacteria within the vaccine in the respiratory tract. For example, the vaccines may be administered by inhalation or intranasal introduction, e.g., using an inhaler, a syringe, an insufflator, a spraying device, etc. While administration of a single dose of between $1\times10^4$ to $1\times10^7$ (e.g., $1\times10^4$, $5\times10^4$, $1\times10^5$, $5\times10^5$, $1\times10^6$, $5\times10^6$, or $1\times10^7$ +/−10, 20, 30, 40, 50, 60, 70, 80, or 90%) live bacteria is typically sufficient to induce protective immunity against developing a *Bordetella* infection such as *pertussis*, one or more (1, 2, 3, 4, or more) additional doses might be administered in intervals of 4 or more days (e.g., 4, 5, 6, or 7 days; or 1, 2 3, 4, 5, 6, 7, or 8 weeks) until a sufficiently protective immune response has developed. The development of a protective immune response can be evaluated by methods known in the art such as quantifying *Bordetella*-specific antibody titers and measuring of *Bordetella* antigen-specific T cells responses (e.g., using an ELISPOT assay). In cases were a vaccine-induced protective immune response has waned (e.g., after 1, 2, 3, 4, 5, 10 or more years from the last vaccination) a subject may again be administered the vaccine in order to boost the anti-*Bordetella* immune response.

EXAMPLES

Methods

Bacterial growth conditions: BPSM is a streptomycin-resistant Tohama I-derived *B. pertussis* strain. BPAL10 was derived from *B. pertussis* BPZE1, a BPSM derivative strain producing inactivated *pertussis* toxin (PTX), no dermonecrotic toxin (DNT) and background levels of tracheal cytotoxin (TCT). *B. pertussis* strains were cultivated at 37° C. for 72 h on Bordet-Gengou (BG) agar (Difco, Detroit, Mich.) supplemented with 1% glycerol, 10% defibrinated sheep blood, and 100 μg/ml streptomycin (Sigma Chemical CO., St Louis, Mo.). Liquid cultures were performed in Stainer-Scholte (SS) medium containing 1 g/L heptakis(2,6-di-o-methyl) b-cyclodextrin (Sigma).

Cell lines: The human pulmonary epithelial cell line A549 (ATCC CCL-185) and the mouse macrophage cell line J774A.1 (ATCC TIB-67) were cultured according to the ATCC guidelines.

Construction of the CyaA-deficient BPZE1 strain: The CyaA-deficient BPZE1 strain, named BPAL10 was obtained by a double homologous recombination strategy. A 999-bp PCR1 DNA fragment encompassing the 989-bp sequence upstream the first nucleotide of the cyaA ORF and the first 10-bp of cyaA was first PCR amplified from purified BPZE1 chromosomal DNA using the primers, 5'-TTTCTAGAGGCGGTGCCCCGGCCTCG-3' (XbaI site underlined) (SEQ ID NO:1) and 5'-TTGAGCTCTCGCAC-CGACGCAACCGGTG-3' (SEQ ID NO:2). Similarly, a 996-bp PCR2 fragment including the 986-bp sequence downstream the STOP codon of cyaA ORF and the last 10-bp of cyaA, was PCR-amplified using the primers 5'-TTGAGCTCAGCGCCGTGAATCACGGCCC-3' (SEQ ID NO:3) and 5'TTAAGCTTAGCAAGGCAACGCCGCCAGC-3' (HindIII site underlined) (SEQ ID NO:4). Both PCR1 and PCR2 fragments were sequentially cloned into plasmid pJQmp200rpsL18 to obtain the pJQ-PCR2-PCR1 construct using XbaI and HindIII restriction sites. BPZE1 bacteria were electroporated with pJQ-PCR2-PCR1 for integration via double homologous recombination at the cyaA locus to obtain the recombinant *B. pertussis* BPAL10.

Southern blot: Chromosomal DNA was extracted and purified from BPZE1 and BPAL10 bacteria using Genomic-tip 100/G Anion-Exchange Resin (Qiagen) and Genomic DNA Buffer Set (Qiagen) according to the manufacturer's instructions. Chromosomal DNA (1 μg) from BPZE1 and BPAL10 was digested with restriction enzymes for 4 h and subjected to 1.5% agarose gel electrophoresis. The agarose gel containing the digested DNA was chemically treated and transferred onto a nitrocellulose membrane (Millipore) according to Roche's DIG application manual. The membrane was UV-fixed for 1 min and equilibrated with 10 ml pre-heated DIG Easy Hyb solution (Roche) at 65° C. for 20 min, with gentle agitation. A digoxigenin (DIG)-labeled probe was amplified using the PCR DIG Probe Synthesis Kit (Roche) according to the manufacturer's instructions. For hybridization, about 5-25 ng/ml of heat-denatured DIG-labeled DNA probe in DIG Easy Hyb solution was incubated with the membrane overnight at 65° C. Detection was performed using alkaline phosphatase (AP)—conjugated anti-DIG antibody (Roche) at a dilution of 1:5000. The membrane was developed using NBT/BCIP AP substrate (Chemicon).

Western blot: Mid- to late exponentially grown bacteria in SS medium (10 ml) were centrifuged at 7000 rpm for 15 min at room temperature. The supernatant was concentrated 10 times using the 30 kDa cut-off Ultra-4 Centrifugal Filter Device (Amicon) following the manufacturer's protocol. The bacterial pellet was re-suspended in 500 μl of ultrapure water. An equal volume of 2× loading buffer [0.125 M TriseHCl (pH 6.8), 10% (w/v) SDS, 10% (v/v) glycerol, 10% (v/v) 2-mercaptoethanol and 1 drop of Bromophenol blue] was added before heating at 95° C. for 10 min. Chromosomal DNA was sheared by passing the suspension 10 times through a 27G needle followed by heating at 95° C. for 15 min prior to analysis by SDS-PAGE using 8% polyacrylamide gels. The proteins were electro-transferred onto nitrocellulose membranes and incubated with mouse anti-CyaA 9D4 monoclonal antibodies (Santa Cruz Inc., US) diluted at 1:1000, anti-FHA monoclonal anti-bodies (National Institute for Biological Standards and Control, UK) diluted at 1:40,000 and anti-PTX monoclonal antibodies (National Institute for Biological Standards and Control, UK) diluted at 1:4000 in Tris-buffered saline containing 0.1% Tween 20 and 2% bovine serum albumin (BSA). Alkaline phosphatase (AP)-conjugated goat anti-mouse IgG secondary antibodies (Sigma) diluted at 1:3000 was used for chromogenic detection of the proteins upon adding the AP substrate (NBT and BCIP reagents, Sigma).

Growth kinetic assay: For in vitro growth kinetics of *B. pertussis* strains, fresh SS liquid medium was inoculated with an exponentially grown culture at an initial $OD_{600\,nm}$ of 0.5. Absorbance at 600 nm of the cultures was monitored over time at the indicated time points.

Mammalian cell infection: Bacteria grown on BG plates for 3 days at 37° C. were scraped, washed once in sterile PBS and resuspended in RPMI or DMEM medium; $2 \times 10^5$ mammalian cells per well were cultured for 2 days in 24-well plate. The bacteria were added to the cells at a multiplicity of infection (MOI) of 20. For adherence assays, the cells were incubated for 1 h at 4° C., washed thrice with PBS to remove non-adherent bacteria, lysed with $H_2O$ and appropriate dilutions were plated for colony counting. For invasion assay, the plates were incubated for 1 h at 37° C. and 5% $CO_2$, washed thrice with PBS and further incubated at 37° C., 5% $CO_2$ with 100 μg/ml gentamycin for 2 h. Cells were washed, lysed and appropriate dilutions were plated for colony counting. Each sample was performed in quadruplicate. Each experiment was repeated twice independently.

Mouse experiments: Specific-pathogen free BALB/c mice were housed in Individual Ventilated Cages. For colonization studies, 3 week-old BALB/c mice (CARE) were intranasally (i.n.) infected with the different *B. pertussis* strains at either $5 \times 10^5$ or $5 \times 10^3$ CFU/mouse. At the indicated time points post-infection, four mice per group were euthanized, and their lungs were aseptically removed and homogenized in PBS. Serial dilutions from individual lung homogenates were plated onto BG agar and the total CFU per lung was determined after 4-5 days incubation at 37° C.

For immunization studies, groups (n=6) of 3-week-old BALB/c mice were i.n. infected with $5 \times 10^3$ CFU in 20 μl of the different *B. pertussis* strains. Bronchoalveolar lavage fluids (BALFs) and sera were collected two months post-immunization from euthanized mice. Individual BALF samples were recovered by injecting 1 ml of sterile PBS into the lungs of sacrificed animals and performing one lavage step. BALFs were then centrifuged, and the supernatant was removed and stored at −20° C. for antibody detection.

For challenge experiments, BPAL10- or BPZE1-immunized ($5 \times 10^3$ or $5 \times 10^5$ CFU/mouse) mice were i.n. challenged one month post-immunization with $5 \times 10^6$ CFU of virulent BPSM strain. They were euthanized at the indicated time points and their lung homogenates were plated for colony counting.

All the animal experiments were repeated at least twice independently.

Antibody determination: The anti-*B. pertussis* antibody responses were measured by enzyme-linked immunosorbent assay (ELISA) using BPSM total cell lysate as coating antigens. Flat 96-well microtiter plates (Corning NUNC) were coated overnight at 4° C. with 50 ml of coating buffer (0.1 M $Na_2CO_3$—$NaHCO_3$, pH 9.6) containing 5 μg/ml of BPSM total cell lysate. The wells were washed thrice with wash buffer (0.1% Tween 20 in PBS), before blocking with blocking buffer (0.1% Tween 20, 2% BSA in PBS) for 1 h at 37° C. The wells were then washed thrice with wash buffer and 50 μl of mouse serum diluted in blocking buffer or neat bronchoalveolar lavage fluids (BALFs) were added to each well. After incubation at 37° C. for 2 h, the plates were washed thrice before adding 50 μl of 1:3000 diluted horseradish peroxidase (HRP)-conjugated goat anti-mouse IgG (H+L) (Bio-rad) and 1:2000 diluted HRP-conjugated goat anti-mouse IgA (Chemicon) secondary antibodies. The plates were again incubated at 37° C. for 1 h followed by three washes. The ELISA was developed by adding 50 μl of o-phenylenediamine dihydrochloride (OPD) substrate (Sigma) to each well and incubating at room temperature for 20 min in the dark. To stop the reaction, 75 μl of 1 M sulfuric acid was added to each well and absorbance at 490 nm was measured using the Biorad model 680 Microplate Reader and recorded with the Microplate Manager 5.2 software (Biorad). Antibody isotyping was performed as described above with 1:3000 diluted HRP-conjugated goat anti-mouse Fcγ Subclass 1, 2a, 2b and 3 specific IgG (Jackson ImmunoResearch).

Intracellular IFNγ staining: Single-cell suspensions were prepared from spleens of naïve, BPZE1-treated and BPAL10-treated mice (5 mice per group). The splenocytes were seeded in 96-well round-bottom plates (Nunc) at a density of $2 \times 10^6$ cells/well in 100 μl RPMI complete medium (RPMI 1640 supplemented with 10% FCS, $5 \times 10^{-5}$ M β-mercaptoethanol, 2 mM L-glutamine, 10 mM HEPES, 200 U/ml penicillin, 200 μg/ml streptomycin). RPMI complete medium (100 μl) containing 20 μg/ml of BPSM whole-cell lysate was added to the splenocytes. For staining of intracellular IFN, Brefeldin A (One ml of BD GolgiPlug, BD Biosciences) was added to the cultures for the last 5 h to prevent secretion of intracellular cytokines. One million cells were labeled with the eFluor-conjugated anti-CD4 antibody (Clone RM4-5; BD Biosciences) for 30 min at 4° C. Cells were then washed and fixed with BD Cytofix/Cytoperm™ Plus Fixation/Permeabilization Kit, according to manufacturer's protocol (BD Biosciences). To label intracellular IFNγ, cells were incubated with allophycocyanin (APC)-conjugated anti-IFNγ antibodies (clone XMG1.2; BD Biosciences) in the presence of saponin for 30 min at 4° C., washed, and analyzed by use of a Cyan flow cytometer using Summit software (Beckman Coulter).

Cytokine measurement: The levels of cytokines in the culture supernatants from re-stimulated splenocytes were measured by using individual detection kits (eBioscience, San Diego, Calif.) according to the manufacturer's instructions. The experiment was repeated three times independently.

Statistical analysis: In the figures, bars represent the means±standard deviations (SD), and averages were compared using a bidirectional unpaired Student's t test with a 5% significance level with, **P≤0.01.

Results: CyaA deletion in BPZE1 strain and phenotypic characterization: An unmarked deletion of the BPZE1 chromosomal CyaA-encoding gene cyaA was obtained by allelic exchange and was confirmed by Southern blot analyses (FIGS. 1A and B). The mutant strain, named BPAL10, did not produce CyaA, as shown by immunoblot analysis (FIG. 1C) and expressed no hemolytic activity, as evidenced by absence of the clearing zone upon growth on blood agar (FIG. 1D). The in vitro growth profile of BPAL10 was comparable to that of the parental strain BPZE1 with exponential growth phase up to 27 h followed by a typical stationary phase where the apparent decrease in $OD_{600}$ readings is due to FHA-mediated clumping of the bacteria. These observations thus indicated that absence of CyaA does not impair the overall in vitro bacterial fitness (FIG. 2A).

An invasion assay was performed using the murine macrophages J774.1. Bacteria and macrophages were incubated at 37° C. and the infected cells were lysed at different time points post-infection for colony counting. The results indicated that intracellular survival of BPAL10 within the macrophages was comparable to that of the parental counterpart BPZE1, with the exception of the last time point (48 h) at which a significantly lower number of BPAL10 bacteria was recovered compared to BPZE1 (FIG. 2B).

The adherence properties of the CyaA deficient mutant to the human pulmonary epithelial cells A549 and to the murine macrophages J774A.1 were analyzed upon incubation of the bacteria with the mammalian cells at 4° C. to prevent internalization. No statistical difference in the adherence capability to both cell lines was noticed between BPZE1 and BPAL10 bacteria (FIG. 2C).

Lung colonization profile: Whether BPAL10 is impaired in the ability to colonize the mouse respiratory tract was assessed. Since young infants are the ultimate target population of novel *pertussis* vaccines, the colonization profile of BPAL10 was monitored in infant (3 weeks old) BALB/c mice. At an administration dose of $5\times10^5$ CFU, BPAL10 displayed a mild but significant decrease in its ability to persist in the lungs of infant mice compared to BPZE1, as evidenced by significantly lower CFUs recovered at day 7 and 10 post-infection (p.i.) (FIG. 2D). This difference was even more pronounced at a lower administration dose of $5\times10^3$ CFU, with a rapid BPAL10 clearance within 7 days p.i., whereas more than 2 $\log_{10}$ CFUs of BPZE1 were still recovered at day 10 pi. (FIG. 2D).

Figure 3:
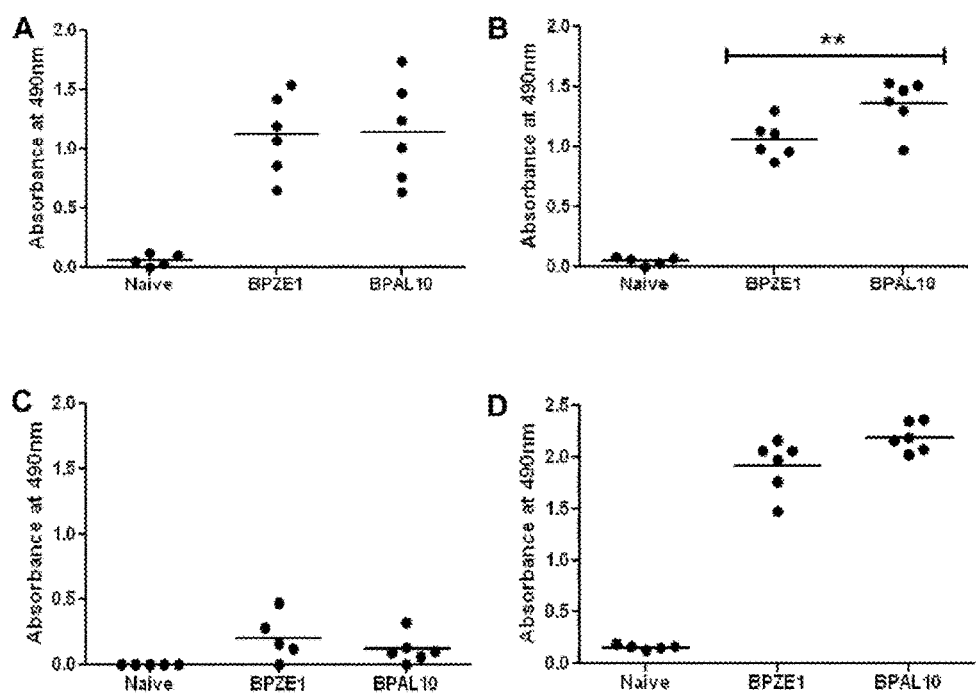
FIG. 3 is a series of graphs showing *B. pertussis*-specific antibody responses in BPAL 10-immunized infant BALB/c mice. Three week-old BALB/c mice were intranasally administered with $5 \times 10^3$ CFU of BPAL10 or BPZE1 as indicated. Bronchoalveolar lavage fluids (BALFs) (A and B) and sera (C and D) were collected 2 months post-infection and total IgA (A and C) and IgG (B and D) antibody responses to *B. pertussis* whole cell lysate were determined by ELISA on individual sera diluted 1/50 and neat BALFs. P values of <0.01 (**) compared to BPZE1-immunized mice were considered significant.

Local and systemic anti-*B. pertussis* antibody responses: Antibody responses against *B. pertussis* infection play an important role in protection, and passive immunization with *B. pertussis*-specific anti-sera reduces disease severity in infected individuals. Furthermore, mucosal IgA in the respiratory tract can inhibit adherence of *B. pertussis* to human ciliated cells. Therefore the local and systemic anti-*B. pertussis* antibody responses in BPAL10-immunized infant mice were measured two months after a single i.n. administration of $5\times10^3$ CFU and compared to the antibody responses measured in BPZE1-immunized age-matched animals. BPAL10-immunized mice produced comparable levels of *B. pertussis*-specific IgA (FIG. 3A) and slightly higher levels of *B. pertussis*-specific IgG antibodies (FIG. 3B) in their BALFs compared to BPZE1-immunized mice. The levels of systemic anti-*B. pertussis* IgG were comparable between the two groups (FIG. 3D), whereas no significant serum IgA response was detected (FIG. 3C).

Mice were i.n. administered with $5\times10^3$ CFU of BPZE1 or BPAL10. Sera were collected 2 months post-infection and analyzed by ELISA for anti-*B. pertussis* IgG1, IgG2a, IgG2b and IgG3. Sera from individual mice of naive group and BPZE1 were pooled, while serum from each BPAL10-immunized mouse was tested individually. Sera from all groups were diluted 1/50 prior to testing. The data presented is representative of two independent experiments. Analysis of the anti-*B. pertussis* IgG subtype indicates that BPAL10-immunized mice produced comparable levels of IgG2a and IgG2b antibodies to those measured in BPZE1-immunized mice, suggestive of a Th1-biased immune response triggered in both animal groups, and demonstrating that the absence of CyaA in BPAL10 did not affect the anti-*B. pertussis* IgG isotype profile (Table 1).

TABLE 1

Anti-*B. pertussis* IgG isotyping in immune sera.
Immunogen Mouse serum Absorbance at
490 nm of serum at 1/50 dilution

|  |  | IgG1 | IgG2a | IgG2b | IgG3 | IgG2aa/IgG1 |
|---|---|---|---|---|---|---|
| Naïve | Pooled | 0.15 | 0.08 | 0.09 | 0.14 | 0.57 |
| BPZE1 | Pooled | 1.21 | 2.68 | 2.96 | 1.27 | 2.22 |
| BPAL10 | M1 | 0.87 | 2.85 | 2.95 | 1.66 | 3.30 |
|  | M2 | 1.68 | 2.89 | 2.95 | 2.15 | 1.72 |
|  | M3 | 1.78 | 2.50 | 2.92 | 2.24 | 1.40 |
|  | M4 | 1.79 | 2.81 | 2.99 | 1.63 | 1.57 |
|  | M5 | 1.19 | 2.67 | 3.14 | 1.33 | 2.25 |
|  | M6 | 1.13 | 2.92 | 2.96 | 0.98 | 2.58 |

Figure 4:
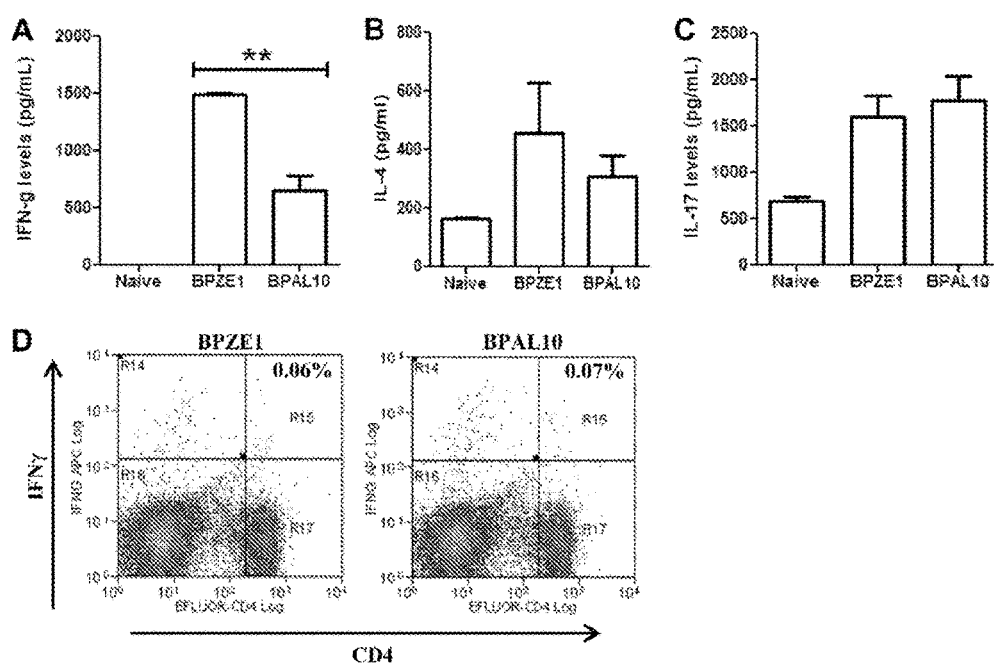
FIG. 4 is a series of graphs and histograms showing cytokine expression profile of BPAL10-primed splenocytes. Three week-old BALB/c mice were intranasally administered with $5 \times 10^3$ CFU of BPAL10 or BPZE1 and their spleens were harvested 2 months post-infection for in vitro re-stimulation with whole cell *B. pertussis* lysate. After 60 h of culture, levels of IFN-γ (A), IL-4 (B) and IL-17 (C) produced in the culture supernatants were quantified by ELISA. The data are expressed as the means±standard errors of the means (SEM) of duplicates and representative of two independent experiments. P values of <0.01 (**) compared to BPZE1-immunized mice were considered significant. (D) Re-stimulated splenocytes were labeled for surface expression of CD4, and stained for intracellular IFNγ expression. The percentages of double positive CD4+ IFNγ+ cells were determined by flow cytometry. Results are representative of three independent experiments.

IFN-γ, IL-4 and IL-17 production: Studies in mice have demonstrated that protection is maintained after waning of circulating antibodies, through the generation of immunological memory. IFNγ plays an essential role in controlling *B. pertussis* infection, and disruption of the gene coding for the IFNγ receptor has been shown to result in an atypical disseminated lethal disease characterized by pyogranulomatous inflammation and post necrotic scarring in the livers, mesenteric lymph nodes and kidneys. Therefore, to assess the IFNγ response of BPAL10-immunized infant mice, their spleens were harvested 2 months post-infection and the splenocytes were re-stimulated in vitro with *B. pertussis* whole cell lysate. Significantly lower levels of IFNγ were measured in the culture supernatant of the re-stimulated BPAL10-primed splenocytes compared to the levels measured in the supernatant of BPZE1-primed splenocytes, with no significant difference in IL-4 and IL-17 (FIG. 4A-C). Whether the reduced IFNγ production by BPAL10-primed splenocytes could be attributed to this cell population was investigated. However, comparable percentages of IFNγ-producing CD4+ T cells were observed in both BPAL10- and BPZE1-primed splenocytes (FIG. 4D) thereby suggesting that the reduced IFNγ production observed with BPAL10-primed splenocytes cannot be attributed to a defective activation of CD4+ T cells.

Figure 5:
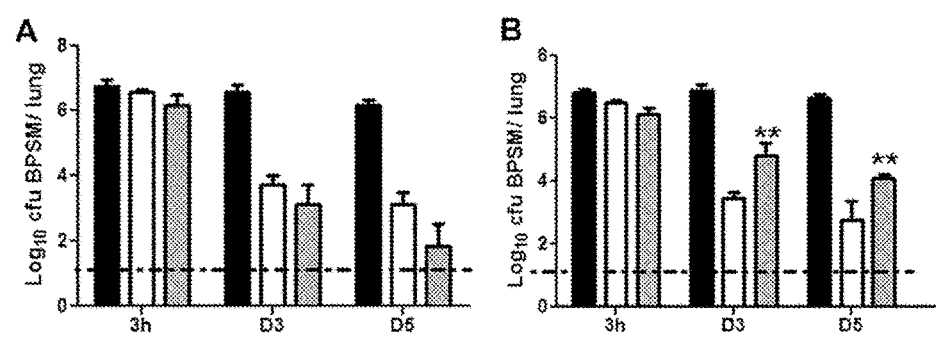

Protective efficacy against *pertussis* challenge: To assess the ability of BPAL10 to protect against subsequent *B. pertussis* infection, 3 week-old BALB/c mice were i.n. infected with either $5 \times 10^5$ or $5 \times 10^3$ CFU of BPZE1 or BPAL10, and challenged with virulent *B. pertussis* BPSM one month later. The results indicate that at $5 \times 10^5$ CFU, a single i.n. immunization with BPAL10 protects as efficiently as BPZE1, as evidenced by a comparable bacterial clearance between the two groups (FIG. 5A). However, with the $5 \times 10^3$ CFU vaccine dose, the BPSM bacterial loads were significantly higher in the BPAL10-immunized mice compared to mice immunized with BPZE1. Thus, these results support that BPZE1 offers a more robust protection to infant mice than its CyaA-deficient counterpart BPAL10 (FIG. 5B).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of immunizing a mammalian subject to protect it from developing *pertussis*, the method comprising the step of colonizing the respiratory tract of a mammalian subject with a vaccine comprising a sufficient amount of a live attenuated *Bordetella pertussis* strain that has been rendered deficient in functional adenylate cyclase toxin (CyaA), functional *pertussis* toxin (PTX), functional dermonecrotic toxin (DNT), and functional tracheal cytotoxin (TCT) to elicit an immune response that prevents the mammalian subject from developing *pertussis*.

2. The method of claim 1, wherein the strain comprises a gene encoding CyaA which has been mutated such that the strain fails to produce CyaA.

3. The method of claim 1, wherein the strain comprises a gene encoding PTX which has been mutated such that the strain fails to produce functional PTX.

4. The method of claim 1, wherein the strain lacks a gene encoding functional DNT.

5. The method of claim 1, wherein the strain lacks a functional wild-type ampG gene.

6. The method of claim 5, wherein the strain comprises a heterologous ampG gene.

7. The method of claim 1, wherein the strain comprises: a gene encoding CyaA which has been mutated such that the strain fails to produce functional CyaA and a gene encoding PTX which has been mutated such that the strain fails to produce functional PTX; and lacks a gene encoding functional DNT, and a functional wild-type ampG gene.

8. The method of claim 1, wherein the strain is BPAL10.

9. The method of claim 1, wherein the vaccine is provided in a single dosage form which comprises at least $5 \times 10^5$ colony forming units (CFU) of the strain.

* * * * *